US012577269B2

(12) United States Patent
Burel et al.

(10) Patent No.: US 12,577,269 B2
(45) Date of Patent: *Mar. 17, 2026

(54) CONTINUOUS PROCESS FOR PREPARING THE CRYSTALLINE FORM II OF SOTAGLIFLOZIN

(71) Applicant: Lexicon Pharmaceuticals, Inc., The Woodlands, TX (US)

(72) Inventors: Bruno Burel, Paris (FR); Jérome Cezerac, Paris (FR); Stéphane Dutheil, Paris (FR); Martial Etienne, Paris (FR); Richard Flacher, Paris (FR); Antonio Nobrega, Paris (FR)

(73) Assignee: LEXICON PHARMACEUTICALS, INC., The Woodlands, TX (US)

(*) Notice: Subject to any disclaimer, the term of this patent is extended or adjusted under 35 U.S.C. 154(b) by 1007 days.

This patent is subject to a terminal disclaimer.

(21) Appl. No.: 17/631,191

(22) PCT Filed: Jul. 31, 2020

(86) PCT No.: PCT/IB2020/057262

§ 371 (c)(1),
(2) Date: Jan. 28, 2022

(87) PCT Pub. No.: WO2021/019509

PCT Pub. Date: Feb. 4, 2021

(65) Prior Publication Data

US 2022/0242897 A1 Aug. 4, 2022

(30) Foreign Application Priority Data

Aug. 1, 2019 (EP) .................................... 19305998

(51) Int. Cl.

| | |
|---|---|
| ***C07H 1/04*** | (2006.01) |
| ***C07H 1/06*** | (2006.01) |
| ***C07H 7/04*** | (2006.01) |
| *C07H 7/06* | (2006.01) |

(52) U.S. Cl.

CPC ................. *C07H 7/04* (2013.01); *C07H 1/06* (2013.01); *C07B 2200/13* (2013.01)

(58) Field of Classification Search

CPC ....................................................... C07H 7/04

See application file for complete search history.

(56) References Cited

U.S. PATENT DOCUMENTS

| | | | |
|---|---|---|---|
| 7,781,577 | B2 | 8/2010 | Harrison et al. |
| 8,026,347 | B2 | 9/2011 | Goodwin et al. |
| 2002/0137903 | A1 | 9/2002 | Ellsworth et al. |
| 2022/0235085 | A1 | 7/2022 | Burel et al. |

FOREIGN PATENT DOCUMENTS

| | | | |
|---|---|---|---|
| CN | 108912080 | A | 11/2018 |
| EP | 3466958 | A1 | 4/2019 |
| JP | 2010504998 | A | 2/2010 |
| JP | 2010534661 | A | 11/2010 |
| JP | 2011528366 | A | 11/2011 |
| JP | 2014501780 | A | 1/2014 |
| JP | 2019516804 | A | 6/2019 |
| JP | 2022543057 | A | 10/2022 |
| WO | 2008042688 | A2 | 4/2008 |
| WO | 2008109591 | A1 | 9/2008 |
| WO | 2010009197 | A1 | 1/2010 |
| WO | 2018067805 | A1 | 4/2018 |

OTHER PUBLICATIONS

Bernstein, J , "Introduction and Historical Background, Conventions for naming polymorphs", Polymorphism in Molecular Crystals, IUCR Monographs on Crystallography 14, p. 8, ISBN: 978-0-19-850605-8 (2002).

Davies, N , et al., "Selective Oxidation of Monosaccharide Derivatives to Uronic Acids", Tetrahedron Letters 34 (7), 118-1184 (1993).

Patent Cooperation Treaty , International Search Report and Written Opinion for PCT/IB2020/057262, 10 pages, dated Aug. 21, 2020.

U.S. Appl. No. 17/631,209, 2022-0235085.

*Primary Examiner* — Layla D Berry

(74) *Attorney, Agent, or Firm* — Viksnins Harris Padys Malen LLP

(57) ABSTRACT

The present document relates to a process for the preparation of the crystalline form II of sotagliflozin from compound of formula (A), said process being continuously performed and comprising at least the steps of: a) performing in a reaction chamber the reaction of said compound of formula (A) in solution in toluene or in xylene or in mixture thereof, and preferably in toluene, and at least sodium methoxide and methanol, at a temperature below the boiling point of methanol, to form sotagliflozin in mixture with sodium salts; b) conducting in a crystallization chamber the crystallization of sotagliflozin formed in step a), in a non-aqueous solvent medium including at least toluene, or xylene or mixture thereof, and free of sodium salts, at a temperature of crystallization of the form II of sotagliflozin; and c) isolating the crystalline form II of sotagliflozin.

17 Claims, 1 Drawing Sheet

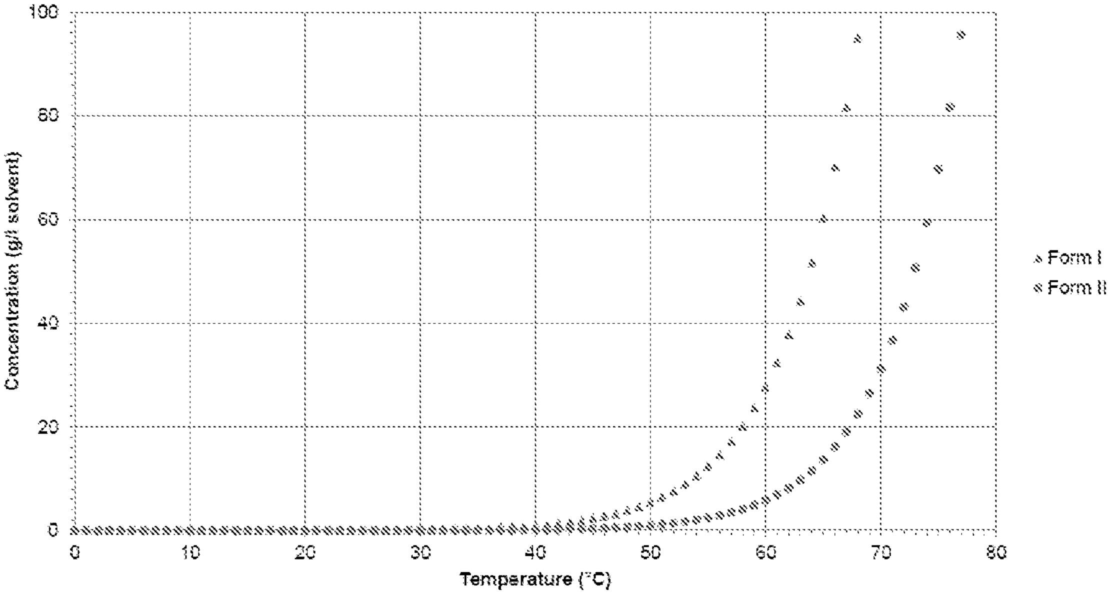
100
80
60
40
20
0
Concentration (g/l solvent)
0
10
20
30
40
50
60
70
80
Temperature (°C)
Form I
Form II

CONTINUOUS PROCESS FOR PREPARING THE CRYSTALLINE FORM II OF SOTAGLIFLOZIN

The present document relates to a new continuous process for preparing the crystalline form II of sotagliflozin.

Sotagliflozin, also called (2S,3R,4R,5S,6R)-2-(4-chloro-3-(4-ethoxybenzyl)phenyl)-6-(methylthio)tetrahydro-2H-pyran-3,4,5-triol or Methyl (5S)-5-[4-chloro-3-(4-ethoxy-benzyl)phenyl]-1-thio-β-L-xylopyranoside, is a drug developed for the treatment of diabetes.

Nowadays, thirteen different forms of sotagliflozin have been identified, and in particular two anhydrous polymorph forms, named class 1 and class 4, corresponding respectively to Form I (crude sotagliflozin) and Form II (pure sotagliflozin).

These forms, and processes for their preparation, have been notably described in WO 2010/009197.

Form I and Form II behave like a monotropic system, the Form II being the most thermodynamically stable.

Form II is therefore the most interesting form of sotagliflozin.

With the current industrial process, Form II of sotagliflozin is produced from a methylthioether derivative in two stages, using a mixture of methanol and water as solvents during the first stage, and a mixture of methylethylketone and heptane during the second stage. The first stage corresponds to the synthesis, crystallization and isolation of Form I of sotagliflozin, and the second stage to the crystallization and isolation of crystalline Form II of sotagliflozin.

The so-obtained crystalline sotagliflozin pure form II, suspended in a methylethylketone/heptane mixture, is in the form of long thin needles. As a result, the medium at the end of crystallization is difficult to stir and the cake after filtration is poorly purged and remains very moist because it still contains 50-60% of solvent.

After drying, on a drying filter, sotagliflozin is in the form of very short broken needles, some forming more or less hard agglomerates.

On an industrial scale, it would be very advantageous that such a process could be performed in a continuous manner.

In effect, continuous flow synthesis has many advantages over conventional batch type synthesis since it may achieve better yield, better purity, reduced cost and better reproducibility.

Thus, it is specifically intended to provide such a process.

BRIEF DESCRIPTION OF THE DRAWINGS

FIG. 1 shows solubility curves of forms I and II of sotagliflozin.

In particular, exemplary embodiments relate to a particular process for the preparation of the crystalline form II of sotagliflozin:

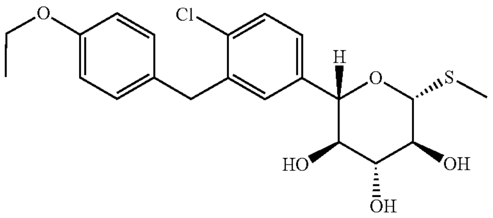 [SMILES: CCOc1ccc(Cc2cc([C@@H]3O[C@H](SC)[C@@H](O)[C@H](O)[C@H]3O)ccc2Cl)cc1]

from the following compound of formula (A):

(A)

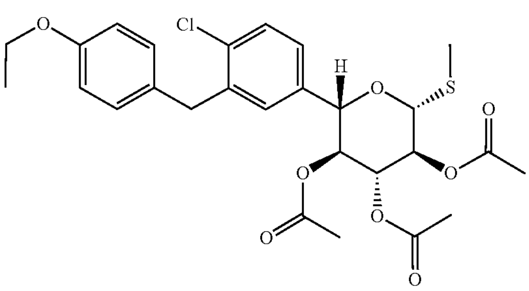

said process being continuously performed and comprising at least the steps of:

a) performing in a reaction chamber the reaction of said compound of formula (A) in solution in toluene or in xylene or in mixture thereof, and preferably in toluene, and at least sodium methoxide and methanol, at a temperature below the boiling point of methanol, to form sotagliflozin in mixture with sodium salts;

b) conducting in a crystallization chamber the crystallization of sotagliflozin formed in step a), in a non-aqueous solvent medium including at least toluene, or xylene or mixture thereof, and free of sodium salts, at a temperature of crystallization of the form II of sotagliflozin; and c) isolating the crystalline form II of sotagliflozin.

"Continuous process" or "Process continuously performed" means a process which can be continued without interruption for feeding and/or removal of involved products, as distinct from "batch process".

Preferably, reaction and/or crystallization chamber(s) is/are continuous stirred-tank reactor(s) (CSTR).

Advantageously, the preparation of the crystalline Form II of sotagliflozin is performed without formation of crystalline Form I of sotagliflozin.

Said process is particularly advantageous over those disclosed in the prior art since it provides Form II of sotagliflozin in good yields and with good chemical purity.

By "good yield", it is meant that said Form II of sotagliflozin is obtained in a yield higher than or equal to 90%.

As used herein a "good chemical purity" is a purity which is higher than or equal to 99%.

Indeed, said process advantageously allows to achieve a clean synthesis. There are no side reactions or degradation in the synthesis leading to the formation of impurities.

Formation of Sotagliflozin: Step a)

The process comprises a step a) of performing in a reaction chamber the reaction of said compound of formula (A) in solution in toluene or in xylene or in mixture thereof, and preferably at least in toluene, and at least sodium methoxide and methanol, at a temperature below the boiling point of methanol, to form sotagliflozin in mixture with sodium salts.

The boiling point of methanol at atmospheric pressure (760 mm Hg) is 64.7° C.

In particular, the process comprises a step a) of promoting in a reaction chamber the reaction of said compound of formula (A) in solution in toluene or in xylene or in mixture thereof, and preferably at least in toluene, and at least sodium methoxide and methanol, at a temperature below the boiling point of methanol, to form sotagliflozin in mixture with sodium salts.

"Promoting" means that the conditions in which the reaction is performed are optimized to facilitate the progress of the reaction.

In said reaction chamber, sotagliflozin is synthesized from the following compound of formula (A):

(A)

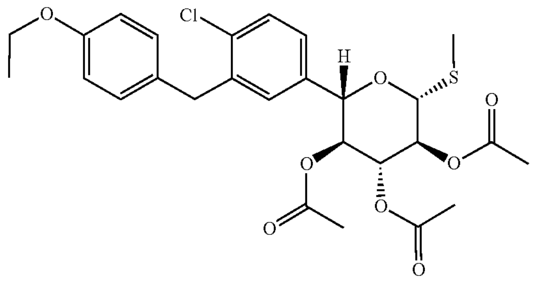

Before reaction, this compound (A) is dissolved in a non-aqueous solvent medium including at least toluene or xylene or mixture thereof, and preferably at least toluene.

A solution of Compound (A) in 10 Volumes of toluene may be notably used.

Toluene or xylene are particularly advantageous since they allow the solubilization of the compound (A) and of sotagliflozin.

Thus, in a preferred embodiment, a first solution of compound (A) in toluene or in xylene or in a mixture of toluene and xylene is prepared. This solution may be heated to completely dissolve compound (A), in particular at a temperature from 25° C. to 45° C., and preferably from 30° C. to 40° C.

Preferably, according to this embodiment, a first solution of compound (A) in toluene is prepared.

The content of toluene may be from 5 to 19 Volumes, in particular from 10 to 19 Volumes, preferably from 10 to 15 Volumes, and more preferably may be of 10 Volumes.

For example, when the first solution of compound (A) is in toluene, the flow of the solution of compound (A) in toluene in the reaction chamber may be from 55 kg/h to 65 kg/h, and in particular from 58 kg/h to 62 kg/h.

It is understood that the flow of the different materials in the chamber(s) may vary according to different parameters, such as, and in non-limiting manner, the volume (diameter/length) of the chamber(s) and the time of residence into the chamber(s). The flow may be set by a skilled man through different routine calculation and/or experiments.

The solution of compound (A) in toluene or in xylene or in a mixture of toluene and xylene is complemented with a solution of sodium methoxide and methanol.

When the first solution of compound (A) is in toluene, the concentration of compound (A) may be comprised from 10 Volumes to 19 Volumes of toluene, and preferably may be equal to 10 Volumes of toluene.

According to this variant, a solution of MeONa and MeOH may be prepared which content of MeONa is at least equal to a catalytic quantity, in particular higher than 0.5 equivalent, preferably higher than 0.6 equivalent, and the content of MeOH is at least equal to a catalytic quantity and preferably is higher than 12 equivalents.

In particular, the content of MeONa is from a catalytic quantity to 1 equivalent, in particular from 0.5 to 1 equivalent, preferably from 0.6 to 1 equivalent, and the content of MeOH is from 12 to 20 equivalents. For example, it can be used 0.6 equivalent of MeONa and 15 equivalents of MeOH.

Said solution of MeONa/MeOH may also be preheated before to be admixed to the solution of compound (A) in toluene, in xylene or in mixture thereof.

"Catalytic quantity" means that the material, such as MeONa or MeOH, is used in a small amount relative to the starting material, i.e. compound (A), but enough to perform the reaction.

For example, the flow of the solution of sodium methoxide and methanol in the reaction chamber may be from 3 kg/h to 8 kg/h, and in particular from 4 kg/h to 6 kg/h.

According to a preferred embodiment, the solution of compound (A) in toluene or in xylene or in a mixture of toluene and xylene, and the solution of sodium methoxide and methanol can be simultaneously fed into the reaction chamber.

Solutions may be driven into the reaction chamber using pumps, such as gear pumps, membrane pumps or peristaltic pumps.

In a preferred embodiment, the temperature in step a) is below 65° C., and preferably below 63° C., at the atmospheric pressure.

More particularly, it is performed at a temperature from 60° C. to 65° C., and preferably from 60° C. to 63° C., at the atmospheric pressure. More preferably, the reaction is performed at 60° C.

Such temperature may be higher in case the reaction is performed under high pressure. For example, the temperature may be around 110° C. if the pressure is at 7-8 bar.

Preferably, the reaction is performed under stirring.

The stirring speed may be set by a skilled man through different routine experiments. It notably depends on the volume of the chamber used.

The time of residence in the reaction chamber is set so as to allow a complete reaction between the compounds. The time of residence may vary according to different parameters, such as, and in non-limiting manner, the temperature of the reaction, the volume (diameter/length) of the chamber, the concentrations of the compounds to be reacted, the flow of the compounds into the chamber. The time of residence may be set by a skilled man through different routine experiments.

In a preferred variant, the time of residence in the reaction chamber is of at least 10 minutes, in particular of at least 15 minutes, preferably of at least 20 minutes and more preferably of at least 30 minutes.

The reaction conducted in the first chamber lead to the formation of a mixture comprising sotagliflozin and sodium salts.

In a preferred variant, the reaction chamber is a continuous stirred-tank reactor (CSTR).

The reaction of step a) may also be performed in an intensified reactor.

According to this variant, the time of residence in the reactor may be advantageously short, for example it may be of at least 20 seconds.

Aqueous Washing and Dehydration

According to a preferred embodiment, the process comprises additional steps between steps a) and b), of removing sodium salts from the medium obtained at the end of step a) by aqueous washing of said medium and followed by dehydration of said medium.

Such step allows removing sodium salts formed during the reaction of compound of formula (A) in solution in toluene, in xylene, or in mixture thereof, and at least sodium methoxide and methanol.

Preferably, the aqueous washing of the medium is performed with 0.5 Volume to 1 Volume of water.

For example, the flow of water may be from 66 kg/h to 79 kg/h, and in particular from 71 kg/h to 75 kg/h.

The temperature during aqueous washing may be from 55° C. to 65° C., and for example be 60° C. Such temperature is advantageous to avoid an intermediate cooling and to prevent the crystallization at this stage of the process.

This step may be performed with a mixer/settler.

The time of residence in the mixer may be of at least 10 minutes, and preferably of at least 15 minutes.

The time of residence in the settler may be of at least 20 minutes, in particular of at least 25 minutes, preferably of at least 30 minutes and more preferably of at least 40 minutes.

Preferably, the aqueous washing is performed under stirring.

The dehydration step is advantageous for preventing the formation of hydrates of sotagliflozin, for avoiding loss of sotagliflozin in methyl acetate and/or methanol in which it is soluble and to remove if present residual solvents, such as methyl acetate and methanol.

The dehydration of the medium is preferably performed by evaporation.

The dehydration may be performed under atmospheric pressure or under reduced pressure.

Preferably, at least 10% v/v, and preferably at least 15% v/v of the solution is evaporated.

Advantageously, the content of water in the medium after dehydration is less than 300 ppm.

Further, after evaporation, the medium is substantially free of methyl acetate and of MeOH.

Preferably, before step b), when toluene is used, the concentration of the toluenic solution may be adjusted from 40 g/l to 80 g/l, preferably from 45 g/l to 50 g/l, and more preferably to 50 g/l. This adjustment may be performed by adding toluene.

Crystallization: Step b)

The process comprises a step b) of conducting in a crystallization chamber the crystallization of sotagliflozin formed in step a), in a non-aqueous solvent medium including at least toluene, xylene, or mixture thereof, and preferably at least toluene, and free of sodium salts, at a temperature of crystallization of the form II of sotagliflozin.

Thanks to the described process, crystalline Form II of sotagliflozin is directly crystallized without formation of Form I of sotagliflozin.

Furthermore, the losses of synthetized crystalline Form II of sotagliflozin in the mother liquors are very low.

The crystallization of sotagliflozin is in particular performed at the temperature of the crystallization of form II of sotagliflozin. The temperature of the crystallization depends on the concentration. It may be chosen based on solubility curves of forms I and II of sotagliflozin as illustrated in FIG. 1.

Preferably, step b) is performed at a temperature from 60° C. to 70° C., preferably from 62° C. to 67° C., and more preferably at 65° C., at the atmospheric pressure.

The solution may be taken to the crystallization chamber by pressure.

In particular, when the solution contains toluene, the content of toluene used during the crystallization may be from 40 g/l to 80 g/l.

For example, the flow of the solution of sotagliflozin in the crystallization chamber may be from 80 kg/h to 90 kg/h.

Preferably, the time of residence in the crystallization chamber is of at least 10 minutes, in particular of at least 15 minutes, preferably of at least 20 minutes, and more preferably of at least 30 minutes.

Preferably, the crystallization is performed under stirring.

According to a preferred embodiment, the formation of the crystalline form II of sotagliflozin is initiated with pre-existing crystalline form II of sotagliflozin. Such pre-existing crystalline form II of sotagliflozin may be synthetized, for example, following the process described in WO 2010/009197.

In particular, the formation of the crystalline form II of sotagliflozin may be initiated with 2% to 15% w/w of pre-existing form II of sotagliflozin, and preferably with 2% to 10% w/w of pre-existing form II of sotagliflozin.

According to this embodiment, the crystallization chamber in step b) is sown with pre-existing crystalline form II of sotagliflozin.

During crystallization, it may be advantageous to implement a wet milling of the medium to stir it easily.

According to this variant, the medium obtained in the crystallization chamber is harvested, subjected to a wet milling, and fed back in said crystallization chamber.

Preferably, the crystallization chamber is a continuous stirred-tank reactor (CSTR).

According to a particular embodiment, step b) is performed in two steps. In the first step, the solution of sotagliflozin is heated to a temperature from 60° C. to 70° C., preferably from 62° C. to 67° C., and preferably at 65° C., at the atmospheric pressure. In the second step, the obtained suspension is cooled at a temperature from 20° C. to 30° C., preferably from 20° C. to 25° C., and preferably at a temperature of 20° C.

Thus, according to this embodiment, the process comprises an additional step b'), between steps b) and c), of feeding a subsequent crystallization chamber with the medium obtained at the end of step b), at a temperature below the temperature of the preceding crystallization chamber.

In particular, the temperature in step b') is from 20° C. to 30° C., preferably from 20° C. to 28° C., and more preferably is 20° C., at the atmospheric pressure.

In this variant, a wet milling may be performed during the first step.

According to this variant, the crystallisation of sotagliflozin may be performed in a cascade of two or more continuous stirred-tank reactors.

Preferably, the crystallisation of sotagliflozin is performed in a cascade of two continuous stirred-tank reactors.

The suspension of sotagliflozin obtained at the end of the first crystallization chamber may thus be taken to the subsequent crystallization chamber, for example with a peristaltic pump.

In this variant, the time of residence in the first crystallization chamber may be of at least 25 minutes, and preferably of at least 30 minutes, and the time of residence in the subsequent crystallization chamber may be of at least 25 minutes, and preferably of at least 30 minutes.

In particular, the flow of the solution of sotagliflozin in the first crystallization chamber may be for example from 80 kg/h to 90 kg/h, and the time of residence in the first crystallization chamber may be of at least 25 minutes, and preferably of at least 30 minutes. The flow of the suspension of sotagliflozin in the subsequent crystallization chamber may be for example from 80 kg/h to 90 kg/h, and the time of residence in the subsequent crystallization chamber may be of at least 25 minutes, and preferably of at least 30 minutes.

Isolation of the Crystalline Form II of Sotagliflozin: Step c)

The process comprises a step c) of isolating the crystalline form II of sotagliflozin.

The isolation of the crystalline form II of sotagliflozin may be advantageously performed at a temperature below 40° C., in particular below 30° C., and preferably at 20° C.

Filtration and Washing

The mixture obtained after step b) or after step b') may be filtrated and washed, preferably with toluene or xylene or mixture thereof, and more preferably with toluene.

During this step, mother and wash liquors are removed.

For example, the flow of the suspension of sotagliflozin for the filtration may be from 80 kg/h to 90 kg/h.

In particular, the filtration of the mother liquors may be performed at a temperature below 40° C., in particular below 30° C., and preferably at 20° C.

Preferably, the resulting wet cake is washed with 2 Volumes of toluene at 25° C.

The filtration may be carried out under vacuum or under high pressure. Preferably, the filtration is carried out under high pressure, for example at 3 bar.

For example, the filtration may be performed on a continuous filter, for example on a rotary pressure filter or on a vacuum band filter.

The washing is carried out with a solvent, for example with toluene or xylene or mixture thereof, preferably with toluene.

Drying

The filtration and washing may be followed with a drying step.

In particular, a drying step is performed at a temperature from 45° C. to 65° C., and in particular from 50° C. to 55° C.

The drying step may be carried out under a pressure below 100 mbar, and in particular below 50 mbar.

In particular, a conical screw dryer or a pallet dryer may also be used for the drying step.

Calibration

In particular, the calibration is carried out at a temperature from 20° C. to 30° C., and preferably at 25° C.

In particular, a conical sieve mill may be used.

This step allows the elimination of clusters formed during the drying step.

The examples that follow describe the preparation of Form II of sotagliflozin. These examples are not limiting and serve merely to illustrate the process.

EXAMPLES

Example 1: Continuous Process of Preparation of Crystalline Form II of Sotagliflozin with Toluene

Synthesis of Sotagliflozin in Toluene

A toluenic solution of compound (A) was prepared with 10 Volumes of toluene, at room temperature (25° C.). The medium was heated at 30-40° C. to completely dissolve compound (A).

0.6 equivalent of MeONa and 15 equivalents of MeOH were used to prepare a methanolic solution of MeONa.

A continuous stirred-tank first reactor, with a volume reactor of 37 l, was fed with both solutions, under stirring of 180 tr/min and at atmospheric pressure. The flow of the toluenic solution of compound (A) was 60.5 kg/h and the flow of the methanolic solution of MeONa was 5.8 kg/h.

The synthesis was performed at 62° C.

The time of residence in the reactor was 30 minutes.

Aqueous Washing

The obtained solution was taken to another reactor with a flow of 66.3 kg/h.

An aqueous wash of the reaction medium was performed, at 60° C.

The wash was performed with 1 Volume of water/reaction medium.

Sodium salts were well removed.

Dehydration

The solution was dehydrated in a reactor by evaporation at 70-110° C., under atmospheric pressure.

Crystallization

The crystallisation of sotagliflozin was performed in a cascade of two continuous stirred-tank reactors.

The solution was taken to the reactor by pressure.

At the beginning, the reactor was sown with 7% w/w of form II of sotagliflozin.

The reactor was fed with the toluenic solution of sotagliflozin (50 g/l) at 65° C., with a flow of 84.9 kg/h, under stirring at 134 tr/min. The time of residence in the reactor was 30 minutes.

The medium obtained in the crystallization chamber was harvested, was subjected to a wet milling, and was fed back in said crystallization chamber.

The suspension of sotagliflozin obtained at the end of the crystallization chamber was taken to another subsequent crystallization chamber.

This reactor was fed with the suspension of sotagliflozin obtained at the end of the previous reactor, at 20° C., with a flow of 84.9 kg/h, under stirring at 134 tr/min. The time of residence in the reactor was 30 minutes.

The suspension obtained at the end of the reactor was recovered for its isolation (filtration, washing, and drying).

Filtration

A filtration of the suspension was performed at 20° C. on a rotary pressure filter, at a pressure of 2.5 bar. The suspension was taken with a flow of 84.9 kg/h.

Washing

A wash of the medium was performed at 20° C. with 2 Volumes of toluene, at a pressure of 2.5 bar. The medium was taken with a flow of 12.5 l/h.

Drying

A drying of the medium was then performed at 55° C. under pressure below 100 mbar.

Form II of sotagliflozin was crystallized with a yield of 97%.

An XRPD (X-ray diffraction) analysis confirmed that Form II of sotagliflozin was obtained.

Example 2: Continuous Process of Preparation of Sotagliflozin with Toluene in an Intensified Reactor Synthesis of Sotagliflozin in Toluene Sotagliflozin was synthetized in an intensified reactor at 113° C. under a pressure of 8 bar.

The reactor was fed with the solution of compound (A) in 10 Volumes of toluene with a flow of 1194.6 g/h and the methanolic solution of MeONa (0.6 equivalent of MeONa and 15 equivalents of MeOH) with a flow of 114.6 g/h, which were preheated at 113° C.

The time of residence in the reactor was 20 seconds.

The system was maintained at a pressure of 8 bar.

Sotagliflozin was synthetized with a yield of 99.7%.

Aqueous washing, dehydration, crystallization, filtration, washing, drying were performed according to example 1.

An XRPD (X-ray diffraction) analysis confirmed that Form II of sotagliflozin was obtained.

The invention claimed is:

1. A process for preparing crystalline form II of sotagliflozin from a compound of formula (A):

(A)

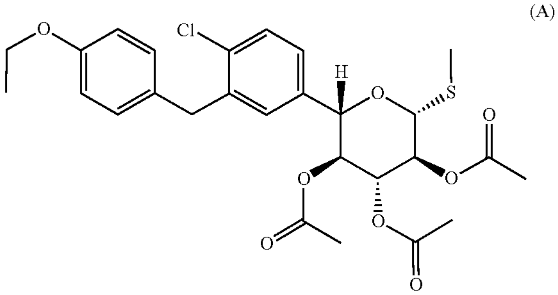 [SMILES: CCOc1ccc(Cc2cc([C@@H]3O[C@H](SC)[C@@H](OC(C)=O)[C@H](OC(C)=O)[C@H]3OC(C)=O)ccc2Cl)cc1]

said process being continuously performed and comprising the steps of:

a) in a reaction chamber, contacting a solution compound of formula with sodium methoxide and methanol under conditions sufficient to form a mixture of sotagliflozin and sodium salts, wherein: the solution comprises the compound of formula (A) and toluene, xylene, or a mixture thereof; and the conditions are at a temperature below the boiling point of methanol;

b) in a first crystallization chamber, crystallizing sotagliflozin in from a non-aqueous solvent medium to provide crystallized form II of sotagliflozin free of sodium salts, wherein the non-aqueous solvent medium comprises toluene, xylene, or a mixture thereof; and c) isolating the crystalline form II of sotagliflozin.

2. The process of claim 1, wherein the solution comprises toluene.

3. The process of claim 1 or 2, wherein the non-aqueous solvent medium comprises toluene.

4. The process of claim 1, wherein the temperature in step a) is below 65° C., at atmospheric pressure.

5. The process of claim 1, wherein the sotagliflozin resides in the reaction chamber for at least 10 minutes.

6. The process of claim 1, which further comprises removing sodium salts from the mixture by aqueous washing of and the mixture followed by dehydration of the mixture.

7. The process of claim 6, wherein the mixture is dehydrated by evaporation.

8. The process of claim 1, wherein the sotagliflozin is crystallized at a temperature of from 60° C. to 70° C. at atmospheric pressure.

9. The process of claim 1, wherein the crystallization chamber in step b) is sown with pre-existing crystalline form II of sotagliflozin.

10. The process of claim 1, wherein the sotagliflozin resides in the crystallization chamber for at least 10 minutes.

11. The process of claim 1, wherein the crystallized form II of sotagliflozin is harvested, wet milled, and fed back into the crystallization chamber.

12. The process of claim 1, further comprising an additional step b'), between steps b) and c), of feeding a second crystallization chamber with the crystallized form II of sotagliflozin obtained at the end of step b), which second crystallization chamber is maintained at a temperature below the temperature of the first crystallization chamber.

13. The process of claim 12, wherein the temperature in step b') is from 20° C. to 30° C., at atmospheric pressure.

14. The process of claim 1, wherein the crystallized form II of sotagliflozin free of sodium salts is filtered and washed with toluene, xylene, or mixture thereof.

15. The process of claim 14, wherein the filtration and washing are followed with drying.

16. The process of claim 15, wherein the drying is performed at a temperature of from 45° C. to 65° C.

17. The process of claim 12, wherein the reaction and/or crystallization chamber(s) is/are continuous stirred-tank reactor(s).

* * * * *